United States Patent

Smith et al.

[11] Patent Number: 6,093,255
[45] Date of Patent: Jul. 25, 2000

[54] METHODS OF SANITIZING MRI MACHINES

[76] Inventors: Sidney D. Smith, 5740 Yellowrose Ct., Columbia, Md. 21045-2500; Joe A. Taylor, 12305 Longwater Dr., Mitchellville, Md. 20721

[21] Appl. No.: 09/314,300

[22] Filed: May 19, 1999

Related U.S. Application Data

[62] Division of application No. 08/761,201, Dec. 6, 1996, Pat. No. 5,918,342.

[51] Int. Cl.⁷ .............................. B08B 9/04; A47L 13/16
[52] U.S. Cl. ..................... 134/8; 134/6; 134/7; 15/244.2
[58] Field of Search ...................... 134/6, 7, 8; 15/244.2, 15/244.1, 244.3, 144.3, 144.1, 144.4, 228, 231

[56] References Cited

U.S. PATENT DOCUMENTS

| | | |
|---|---|---|
| 57,460 | 8/1866 | Barnard . |
| 361,502 | 4/1887 | Gibson . |
| 698,527 | 4/1902 | Lurtz . |
| 1,420,714 | 6/1922 | Lee . |
| 2,037,870 | 4/1936 | Whisler et al. . |
| 2,205,379 | 6/1940 | Agostineto . |
| 2,432,924 | 12/1947 | Nishizaka et al. . |
| 2,930,059 | 3/1960 | Frank ..................................... 15/104.18 |
| 3,142,855 | 8/1964 | Gilchrist ................................. 15/244.1 |
| 3,188,676 | 6/1965 | Zelinski et al. ......................... 15/119.2 |
| 3,205,520 | 9/1965 | Trentel ................................... 15/119.2 |
| 4,475,262 | 10/1984 | Downer .................................. 15/144.2 |
| 4,562,608 | 1/1986 | Weir ....................................... 15/163 |
| 4,712,268 | 12/1987 | Heinonen ................................ 15/231 |
| 4,971,471 | 11/1990 | Sloan ...................................... 15/228 |
| 5,343,587 | 9/1994 | Findley ................................... 15/228 |
| 5,384,929 | 1/1995 | Smith .................................. 15/104.061 |
| 5,457,841 | 10/1995 | Minton ............................... 15/104.061 |
| 5,596,787 | 1/1997 | Stevens et al. .......................... 15/228 |

FOREIGN PATENT DOCUMENTS

| | | | |
|---|---|---|---|
| 263480 | 11/1949 | Switzerland ............................ 15/231 |
| 774537 | 10/1980 | U.S.S.R. . | |
| 920057 | 3/1963 | United Kingdom .................. 15/244.1 |

*Primary Examiner*—Zeinab El-Arini
*Attorney, Agent, or Firm*—Millen, White, Zelano & Branigan

[57] ABSTRACT

A method of sanitizing the bore of an MRI machine by using a pair of sponge elements attached to an elongated handle. The first sponge element has an arcuate surface which is a segment of a sphere having a radius substantially equal to the radius of the bore, the arcuate surface having a first dimension longer than a second dimension. The first sponge element is mounted on an elongated handle having axis which is transverse to the first dimension of the sponge element when the sponge element is used for sanitizing the ceiling of some bores. According to the method, a second sponge element with a planar surface is used for cleaning the floor or track of the bore and disposable cleaning are provided for mounting on the sponge element.

4 Claims, 11 Drawing Sheets

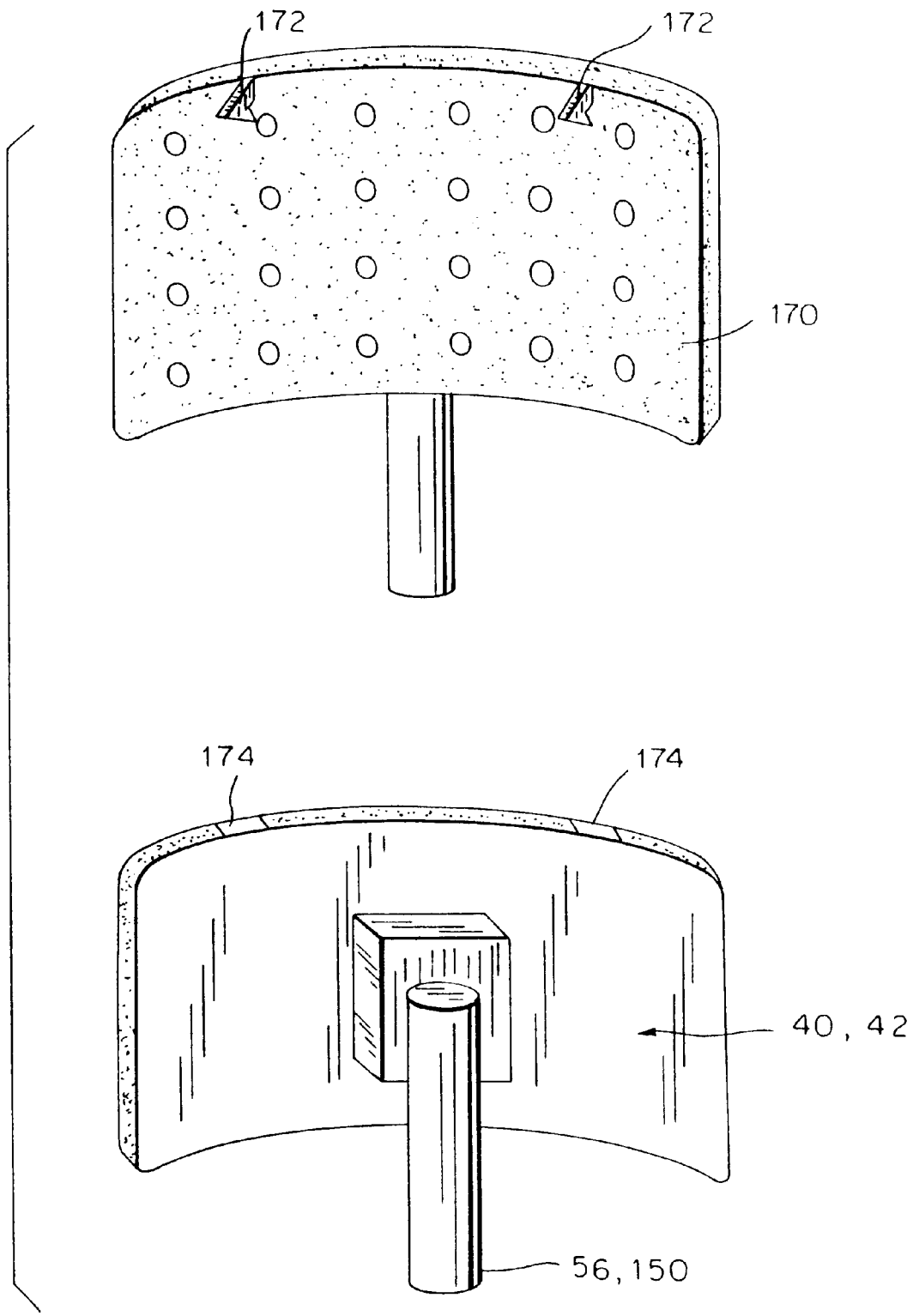
F I G. 15

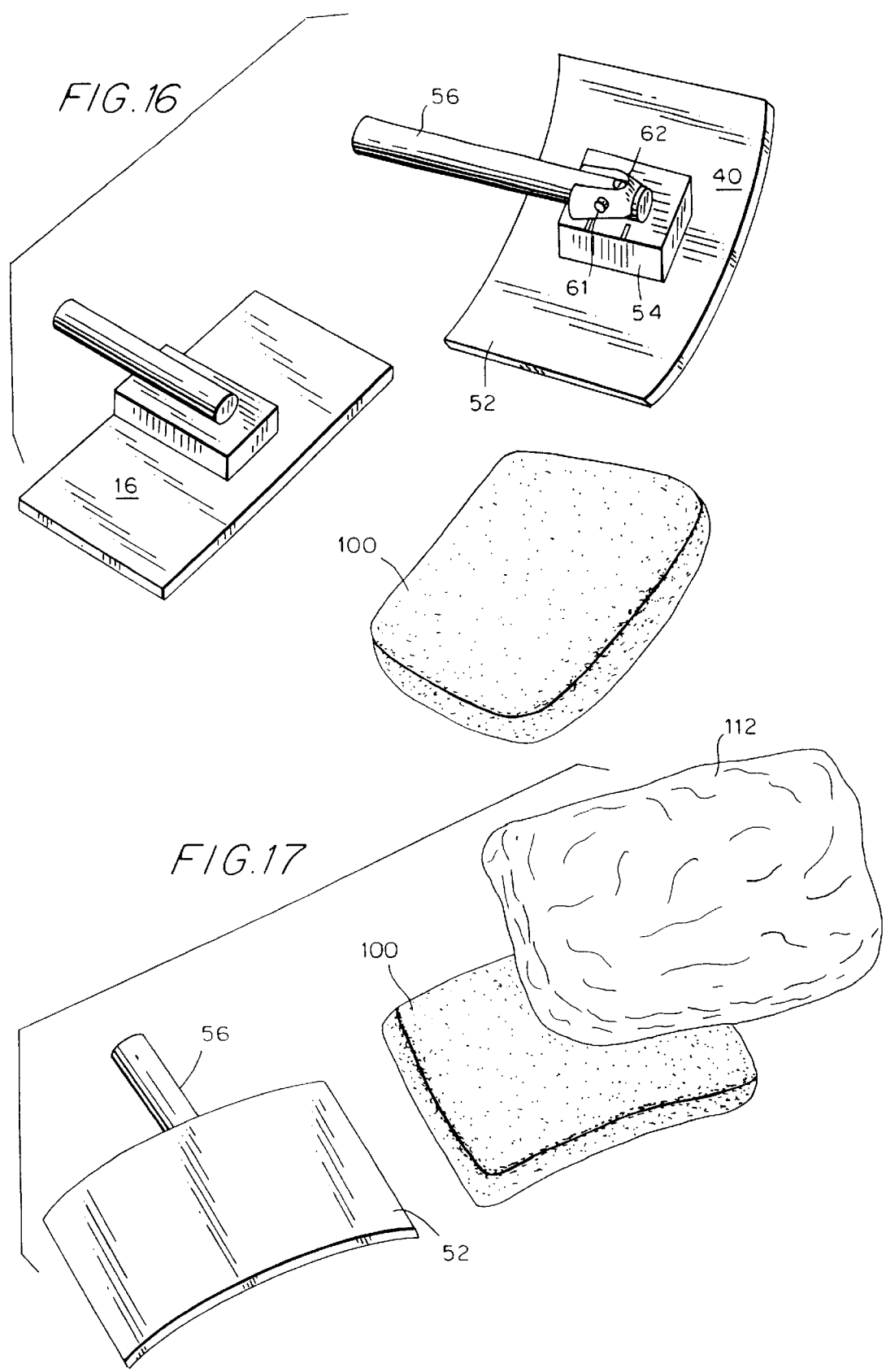

METHODS OF SANITIZING MRI MACHINES

This is a divisional of application Ser. No. 08/761,201 filed Dec. 6, 1996, now U.S. Pat. No. 5,918,342.

FIELD OF THE INVENTION

The present invention relates to methods of and apparatus for sanitizing MRI machines. More particularly, the present invention relates to methods of and apparatus for sanitizing MRI machines utilizing devices for applying disinfectant substances thereto.

BACKGROUND OF THE INVENTION

Magnetic resonance imaging machines (MRI machines) are now used extensively in hospitals and MRI centers in order to enable physicians to view cross-sections of patients' anatomy. These machines are very expensive to purchase and cost in the range of $2 million dollars each, depending on field strength. In order to rapidly recover the expense of this investment, the desired practice is to use these machines 8–24 hours a day, cycling patients in and out of the machines in increments of about 1 hour or less. With currently available software, the cycle time has been reduced to about 25 minutes. In addition to the pressure imposed by the need to recover the large initial investment, there is pressure to utilize the machines as much and as quickly as possible since each MRI scan costs a patient or insurer in the neighborhood of $1000, not including a radiologist's fee of $250 to $300. Accordingly, any time that the machine is not being used, it appears that the organization owning or leasing the machine is losing money.

The medical problems confronting patients scanned by MRI machines cover the gambit from fractured bones to cancer, from AIDS to tuberculosis. The environment of an MRI machine is friendly to infectious agents because the bore has a diameter in the range of 54 to 60 cm, and can become warm and with an environment which promotes a bacteria growth. Since patients remain in the machine for 25 to 45 minutes while breathing and perhaps perspiring, these machines can become coated with bacteria and viruses. On occasion, patients sneeze, cough, vomit, urinate or defecate while confined in the bore of an MRI machine. While these events may not be injurious to the technologist performing them, subsequent patients may find themselves in substantial peril. For example, a patient's gown could be wet from their own urine and coat the wall of the bore which could unknowingly transmit a disease to the next patient.

This peril poses a substantial health problem. Recognizing the problem creates a reason to develop a protocol for sanitizing MRI machines.

Still, the problem remains and is readily apparent to the health care technologists who operate the machines and observe and cope with the infectious events.

Occasionally, patients may find themselves in the bores of MRI machines proximate readily apparent residue of previous infectious events which residue has not been removed by a technologist. They will then complain vehemently of the situation in which they find themselves. The scanning procedure must then be terminated, the patient withdrawn from the bore and the visible, noxious material removed before the patient can be reintroduced into the bore. Having been previously revolted, it may be difficult to persuade the patient to reenter the bore. This, of course, can disrupt scheduling. When a patient causes a major infectious event, it may take 15 or 20 minutes to clean the MRI machine, requiring the MRI technologist or some other unfortunate employee to climb into the bore in order to clean the bore which, to say the least, increases the chance of the technologist contracting a disease.

For the foregoing and other reasons, it is a feature of the present invention to provide methods and apparatus for sanitizing MRI machines after each patient has been scanned, or at least when obviously necessary.

SUMMARY OF THE INVENTION

It is a feature of the present invention to sanitize the bores of MRI machines.

In its broadest aspect, the present invention is directed to a method and apparatus for sanitizing the bores of an MRI machine after scanning a patient so that the bore is sanitary prior to scanning a subsequent patient. Disposable covers are used on a cleaning implement which covers are replaced after use, preferably after each use.

In a more specific aspect, the present invention is directed to an apparatus for sanitizing the bore of an MRI machine wherein the bore has a radius "R" and wherein the apparatus comprises a cleaning element, a mounting plate and an elongated handle. The cleaning element has an application surface thereon which is a segment of a sphere wherein the sphere also has a radius "R". The segment has a first dimension and a second dimension oriented normal to the first dimension, wherein the first dimension is longer than the second dimension. The mounting plate is provided for mounting the sponge element thereon, while the handle is attached to the mounting plate. The handle has an axis which extends transversely with respect to the application surface of the sponge element. All components of the apparatus are made of a non-ferrous material.

In a still more specific aspect, some bores include a relatively narrow ceiling portion defined between a pair of spaced, longitudinally extending ribs. A pivot is provided between the handle and the mounting plate. The pivot allows the mounting plate to rotate with respect to the axis of the handle from a position for sanitizing side walls of the bore to a position for sanitizing the ceiling portion of the bore.

In a further aspect, the first sponge element is removed and replaced with a second sponge element having a planar application surface for applying sanitizing liquid to the floor of the bore.

Another aspect of the invention is directed to a method of sanitizing the bore of an MRI machine, comprising: applying a sanitizing liquid to the arcuate side surfaces of bore with a first cleaning element mounted on an elongated handle, wherein the cleaning element has an application surface configured as a section of a sphere having a radius equal to the radius of the bore.

In a more specific aspect of the method, the sponge is rotated 900 and the sanitizing liquid is applied to the ceiling of the bore after the sponge has been rotated 90°.

BRIEF DESCRIPTION OF THE DRAWINGS

Various other features and attendant advantages of the present invention will be more fully appreciated as the same becomes better understood when considered in conjunction with the accompanying drawings, in which like reference characters designate the same or similar parts throughout the several views, and wherein:

FIG. 15 is an exploded perspective view showing a squeeze plate for compressing the first or second sponge elements to remove liquid therefrom if it is necessary to rinse or otherwise treat the sponge element;

FIG. 16 is a photograph of the first and second cleaning implement heads of the present invention; and FIG. 17 is a photograph of the first cleaning implement head according to the present invention showing the head disassembled with a sponge element, cleaning cover and mounting plate with socket shown separately.

DETAILED DESCRIPTION

Figure 1:
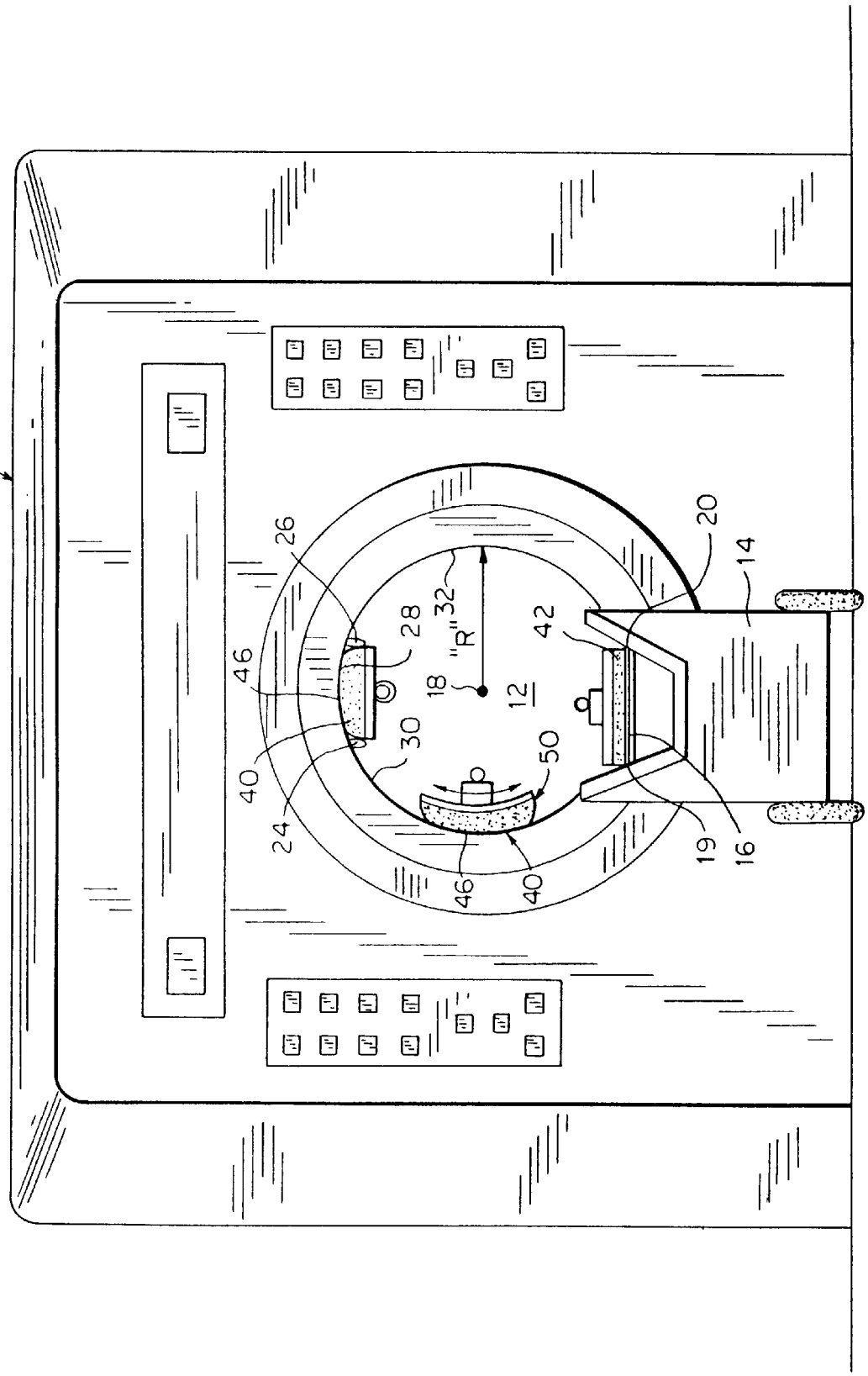
FIG. 1 is an end view of an MRI machine showing cleaning implements configured in accordance with the principles of the present invention used therewith.

Referring now to FIG. 1, there is shown a magnetic resonance imaging machine (MRI) 10 which has a bore 12 therein which receives a patient (not shown). The patient is aligned with the bore 12 by a gurney 14 and is placed on a carriage (not shown) that is advanced through the bore on a horizontal track 16. The bore 12 has a constant radius R measured from the bore axis 18. The radius R is constant from one side 19 of the track 16 to the other side 20 thereof where the track 16 generally defines a planar horizontal surface having cogs (not shown) which engage the carriage (not shown) to advance the carriage and thus the patient through the bore 12.

The bore 12 has ribs 24 and 26 which mount lamps that extend horizontally in the direction of axis 18 of the bore in order to illuminate the bore. There is an arcuate "ceiling" between the ribs 24 and 26 which arcuate ceiling 28 has the radius R. Between the rib 24 and the edge 19 of the track 16 is a first arcuate wall portion 30 and between the rib 26 and second edge 20 of the track is a second arcuate wall portion 32. By utilizing the implements and systems of the present invention, the arcuate walls 30 and 32, the arcuate ceiling 28 and the horizontal track 16 are sanitized after a patient has been scanned in the bore 12 in order to remove infectious agents therefrom.

As is seen in FIG. 1, sanitizing the arcuate walls 30 and 32, the arcuate ceiling 28 and the horizontal track 16 is accomplished by using a first cleaning element 40 and a second cleaning element 42. The first cleaning element 40 cleans both the arcuate side walls 30 and 32 and the arcuate ceiling 28 while a second cleaning element 42 sanitizes only the horizontal track 16 which is substantially planar. As will be explained more fully hereinafter, the first cleaning element has a surface 46 which is a segment of a sphere having a radius R. Accordingly, the surface 46 is arcuate in all directions. When the first cleaning element 40 is oriented for cleaning the side walls 30 and 32, the arcuate surface 46 conforms to the arc of the walls 30 and 32. When the first cleaning element 40 is cleaning the ceiling 28 between the ribs 24 and 26, the first cleaning element is rotated 90° but still presents a surface 46 with an arc having the radius R.

Figure 2:
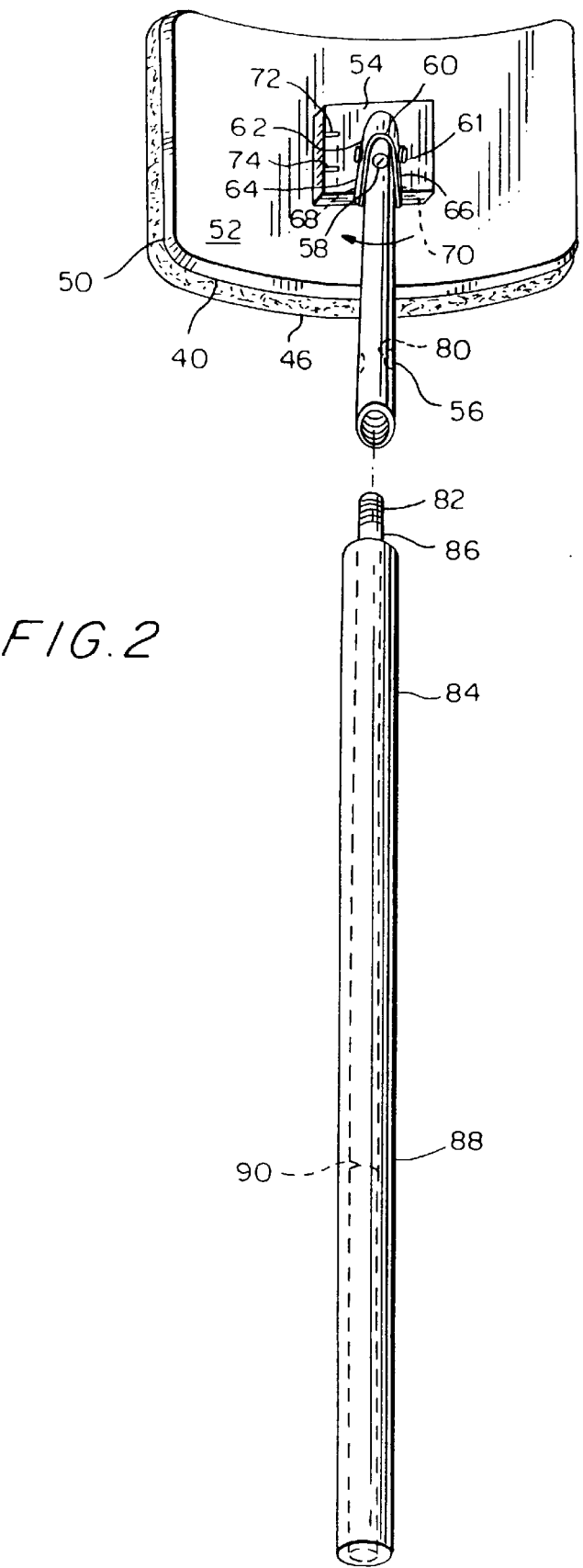
FIG. 2 is a back view of a first cleaning implement of the present invention with a handle attached thereto.

Referring now to FIG. 2, the cleaning element 40 from a cleaning head 51 is attached to a mounting plate 52 which is arcuate and is a segment of a cylinder having the radius R. Projecting from the mounting plate 52 is a boss 54. The boss 54 has a socket 56 pivoted thereto by a pivot pin 58, which pivot pin 58 extends perpendicularly from, or in a radial direction from, the plate 52. The pin 58 restrains the socket 56 to rotation about an axis 60 which extends perpendicular to the void of FIG. 2 (see FIGS. 9 and 10) but prevents the socket from rotating toward the axis 60. In other words, the socket 56 always extends substantially perpendicular to the axis 60.

Pivotally mounted on the socket 56 by a bolt 61 is a latch 62 which has two detent arms 64 and 66 which are received in the first slots 68 and 70 when the socket 56 is in the orientation shown in FIG. 2 and in second slots 72 and 74 when the socket 56 is rotated to a second position in which the socket extends in a direction perpendicular to the direction shown in FIG. 2.

The socket 56 has a threaded nut 80 therein which receives the threaded end 82 of a telescoping handle 84. The telescoping handle 84 includes an inner shaft 86 which has the threads 82 thereon and an outer tube 88 which receives the inner shaft. The inner shaft 86 has an eccentric 90 thereon, so that when the tube 88 is rotated with respect to the shaft 86, the tube and shaft lock with respect to one another. In this way, the length of the handle telescoping 84 is adjusted and locked. As will be further explained hereinafter, it is necessary to be able to rapidly detach the handle 84 from the first head 50 so that a second cleaning head adding the cleaning element 42 thereon may be substituted for the first head.

Figure 3:
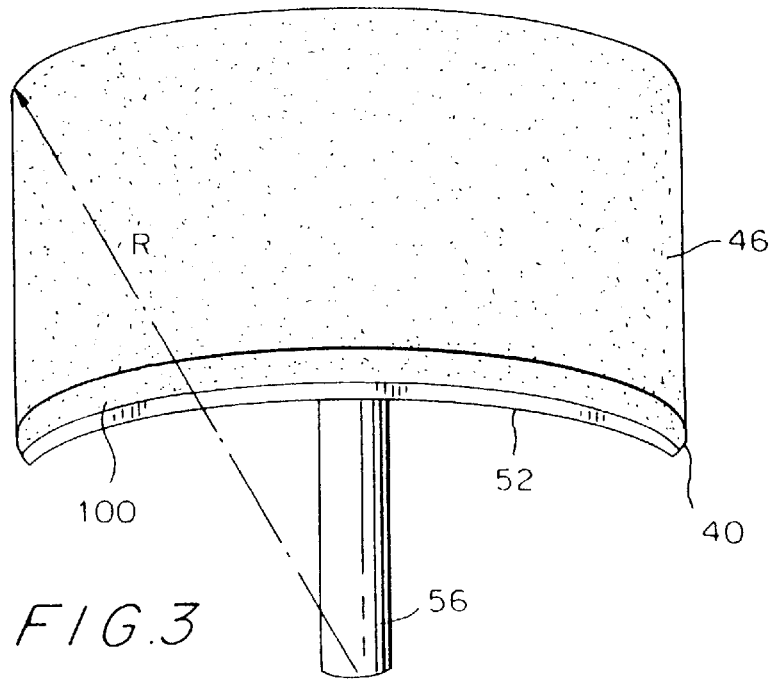
FIG. 3 is a front view of the cleaning implemented in accordance with the present invention with the handle detached.
Figure 4:
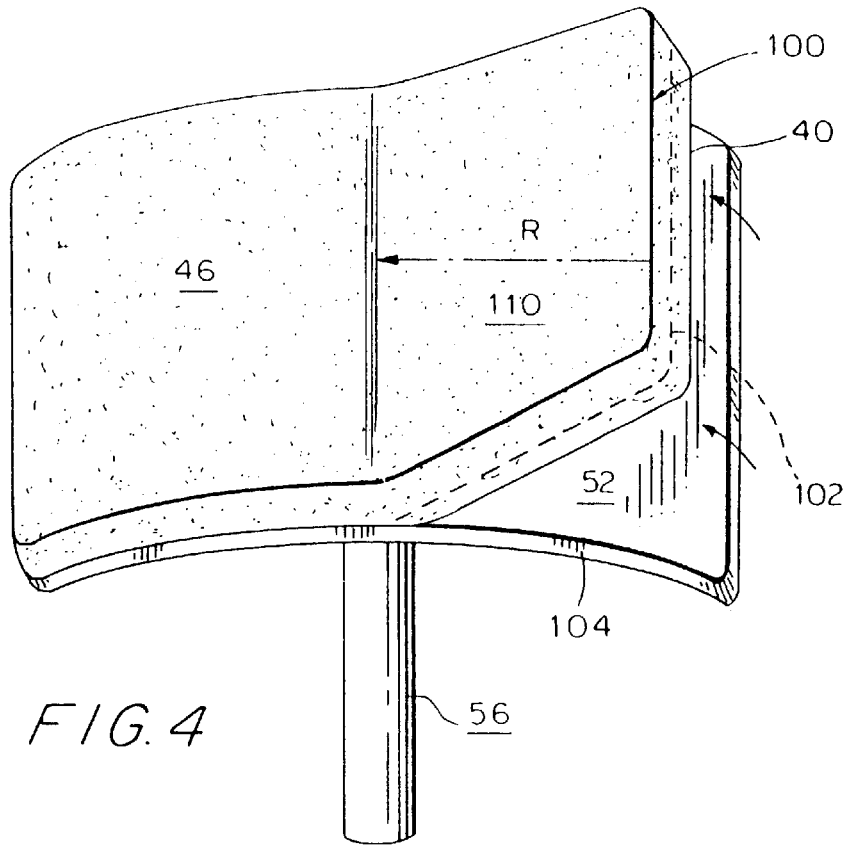
FIG. 4 is a front view showing a sponge section of the cleaning implement being separated from a mounting plate.

Referring now to FIGS. 3 and 4, it is seen that the cleaning element 40 is comprised of a resilient sponge element 100 wherein the sponge element has a radius R which is perpendicular to the extent of the socket 56 when the sponge element 100 is secured to the mounting plate 52. Since the mounting plate 52 has a radius R, the resulting surface 46 of the cleaning element 50 has the shape of a segment of a sphere. As is seen in FIG. 4, the sponge element 100 has a first Velcro® perimeter area 102 made of Velcro® hooks which is releasably adhered to a second Velcro® perimeter area 104 loops fixed to the mounting plate 52. Thus, the sponge element 100 may be pressed onto and retained by the mounting plate 52.

Figure 5:
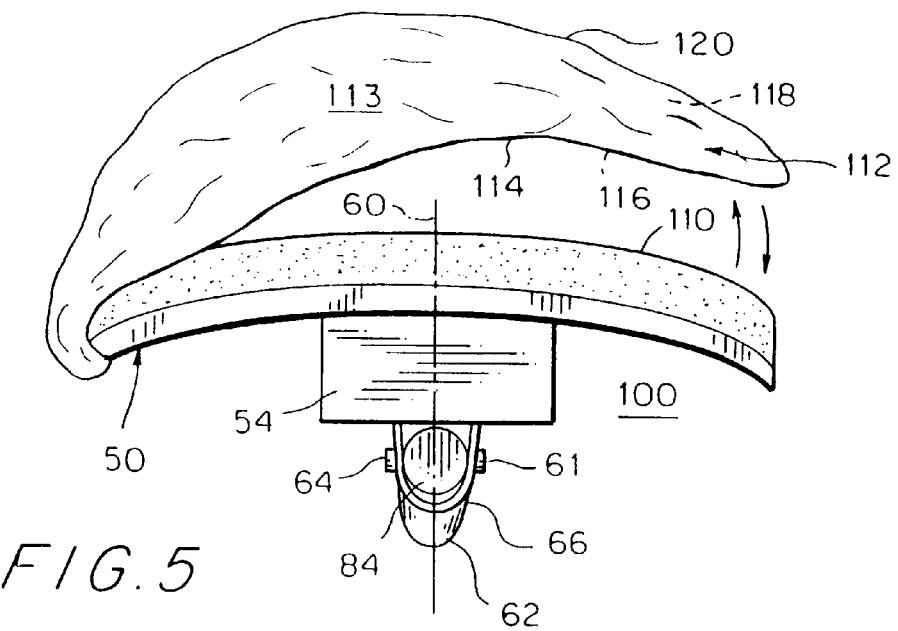
FIG. 5 is an end view showing a cleaning cover being removed from the sponge element of FIG. 4.
Figure 6:
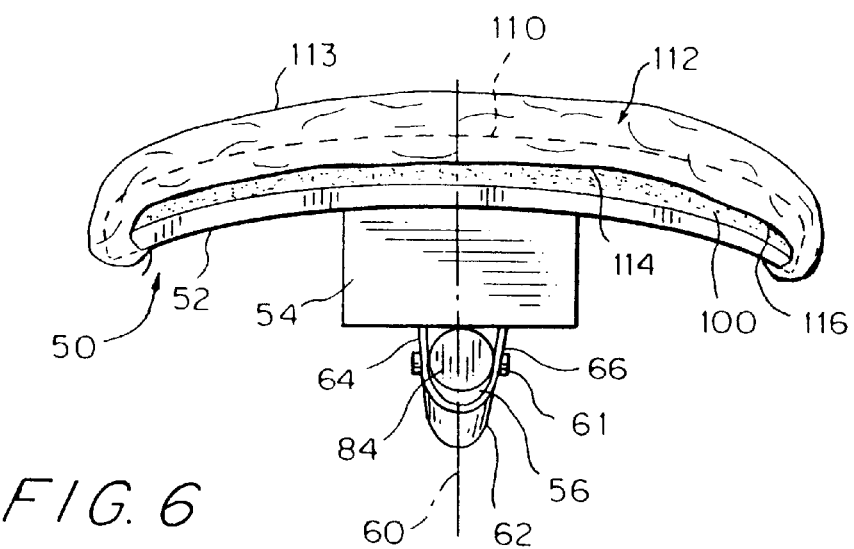
FIG. 6 is a view similar to FIG. 5 but showing the cleaning cover in place on the sponge element.

In a preferred embodiment, the sponge element 100 has a layer of liquid impervious plastic 110 disposed thereon so that the sponge element 100 does not become wet. As is seen in FIGS. 5 and 6, over the layer of impervious plastic 110 there is removably disposed a disposable wiping cloth 112 having a cloth or paper surface layer 113. The wiping cloth 112 has an edge 114 with an elastic band 116 disposed therein. Preferably, the wiping cloth 112 is lined with an impervious layer 118 beneath the cloth or paper surface layer 113 so that liquid on the wiping cloth does not pass therethrough but remains on and in the cloth or paper surface portion of the wiping cloth. Preferably, the cloth or paper layer 113 and the impervious plastic barrier 118 is biodegradable so that when the wiping cloth 112 is disposed of, environmental impact is minimized.

Preferably, the wiping cloth 112 is replaced after each use while the sponge 100 is replaced periodically due to wear and tear. For example, the sponge 100 may be replaced after every one hundred to two hundred uses or perhaps upon the fluid impermeable barrier 110 rupturing.

Figure 7:
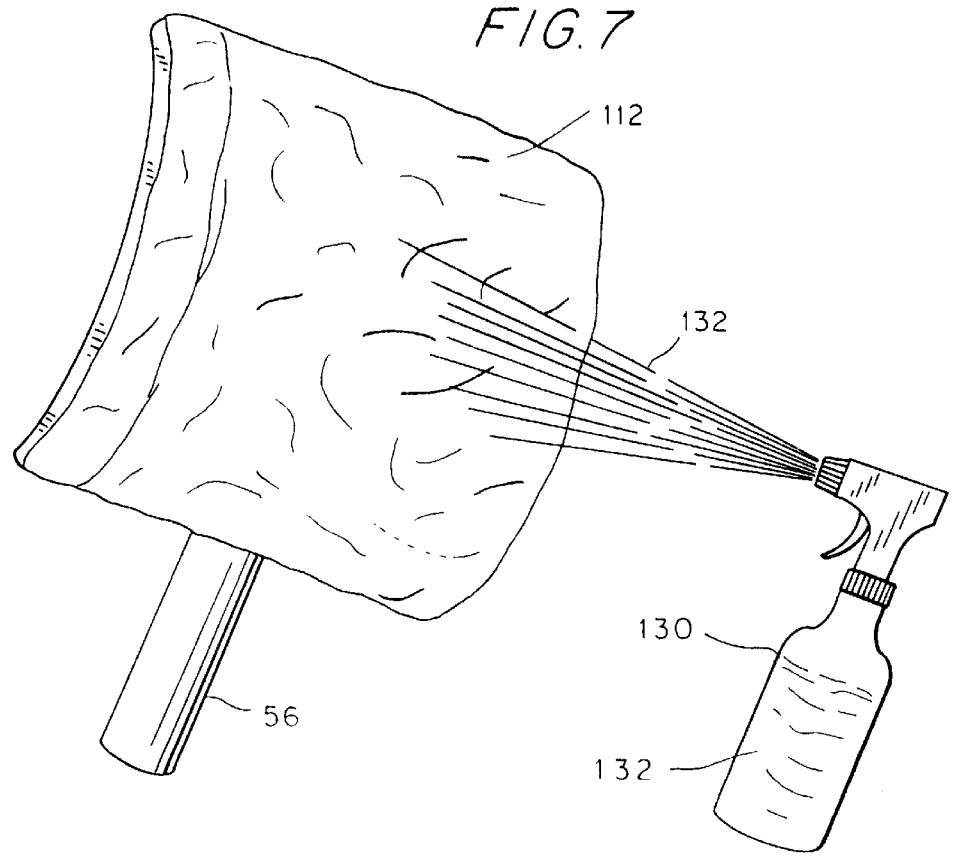
FIG. 7 is a perspective view showing the cleaning cover being treated with a cleaning fluid.

Referring now to FIG. 7, there is shown a spray bottle 130 with a disinfectant 132 therein. The disinfectant 132 is sprayed onto the disposable cleaning cloth 112 prior to swabbing the wall surfaces of the bore 12. By spraying the disinfectant 132 onto the cleaning cloth 112, an adequate but minimal amount of disinfectant 132 is applied to the walls 30, 32 and 28 of the bore 12 to disinfect the bore 12 without leaving an excessive residue in the bore which might have to be wiped out before introducing the next patient for scanning. What residue there is of the disinfectant 132 will remain on the walls of the bore 12 and perhaps inhibit the cultivation of infectious agents which may be released in the bore 12 by the next patient. In any event, when the cover 112 is disposed of in an appropriate sanitary fashion, infectious agents picked up by the cover have, in all likelihood, have been destroyed by the disinfectant 132. The use of a subsequent cover 112 sprayed with the disinfectant 132 disrupts any chain of infectious activity which might occur by virtue of the swabbing process itself.

Figure 8:
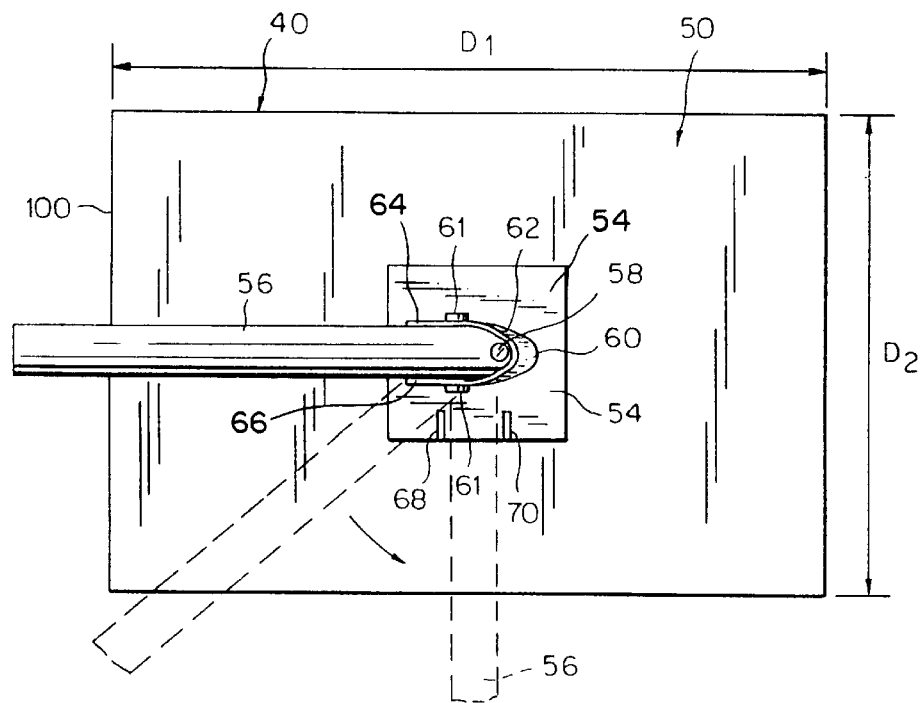
FIG. 8 is a back view of the first cleaning implement showing how a handle is moved from a first position to a second position for configuring the cleaning element for cleaning the ceiling and side walls of the bore of an MRI machine.
Figure 9:
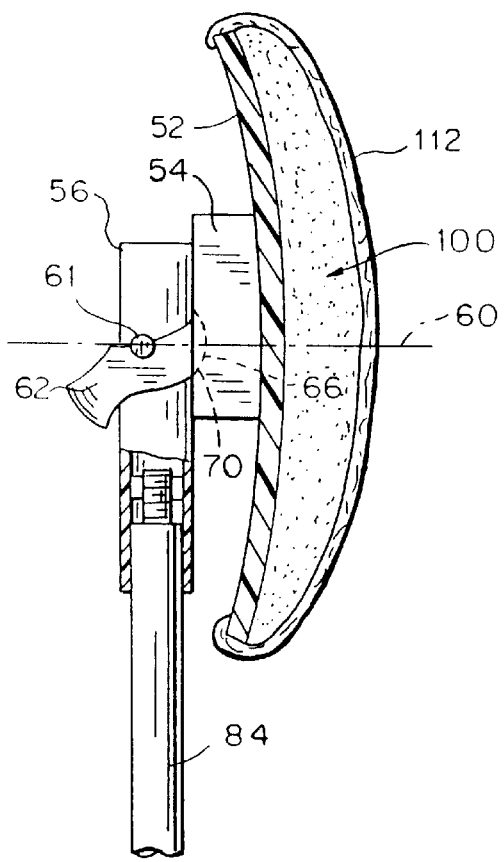
FIG. 9 is a view showing a latching detent in latched position on the first cleaning implement.
Figure 10:
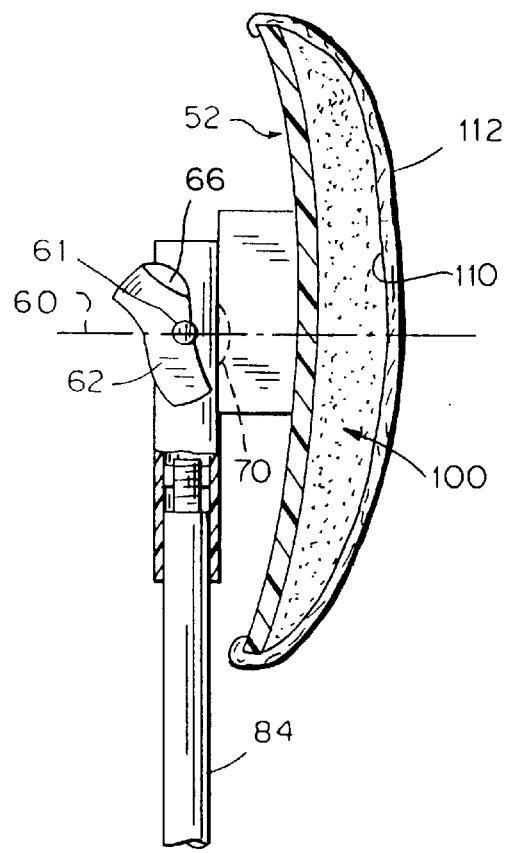
FIG. 10 is a view similar to FIG. 7, but showing the latching detent in an unlatched position.

Referring now to FIGS. 8, 9 and 10, it is seen that the socket 56 receiving the telescoping handle 84 is latched in one of two positions by the latch 62. In the solid line position of FIG. 8, the long dimension D1 of the first cleaning element 40 extends parallel with the axis of the handle 84 for cleaning the ceiling 28 of the bore 12. When the handle 84 is rotated and then latched in the dotted line position of FIG. 8 so that it extends parallel to the short dimension D2 and perpendicular to the long dimension D1, the first cleaning head 40 is used to clean the side walls 30 and 32.

Referring now specifically to FIGS. 9 and 10, it is seen that the latch 62 which is pivoted by pivot pin 63 or the socket 56 has the detent portion 66 in engagement with the slot 70 (and the detent portion 64 in the slot 68) so that the socket 56 and the handle 84 will not rotate with respect to the mounting plate 52. Consequently, the resulting cleaning implement 50 functions as single piece. In FIG. 10, the latch 62 has been rotated counter-clockwise to withdraw the detents 66 and 64 from the slots 68 and 70 which frees the socket 56 and attached handle 84 to rotate to the position where the detents 66 and 64 engage the slots 72 and 74 to provide the ceiling cleaning mode of FIGS. 2 and 8.

Figure 11:
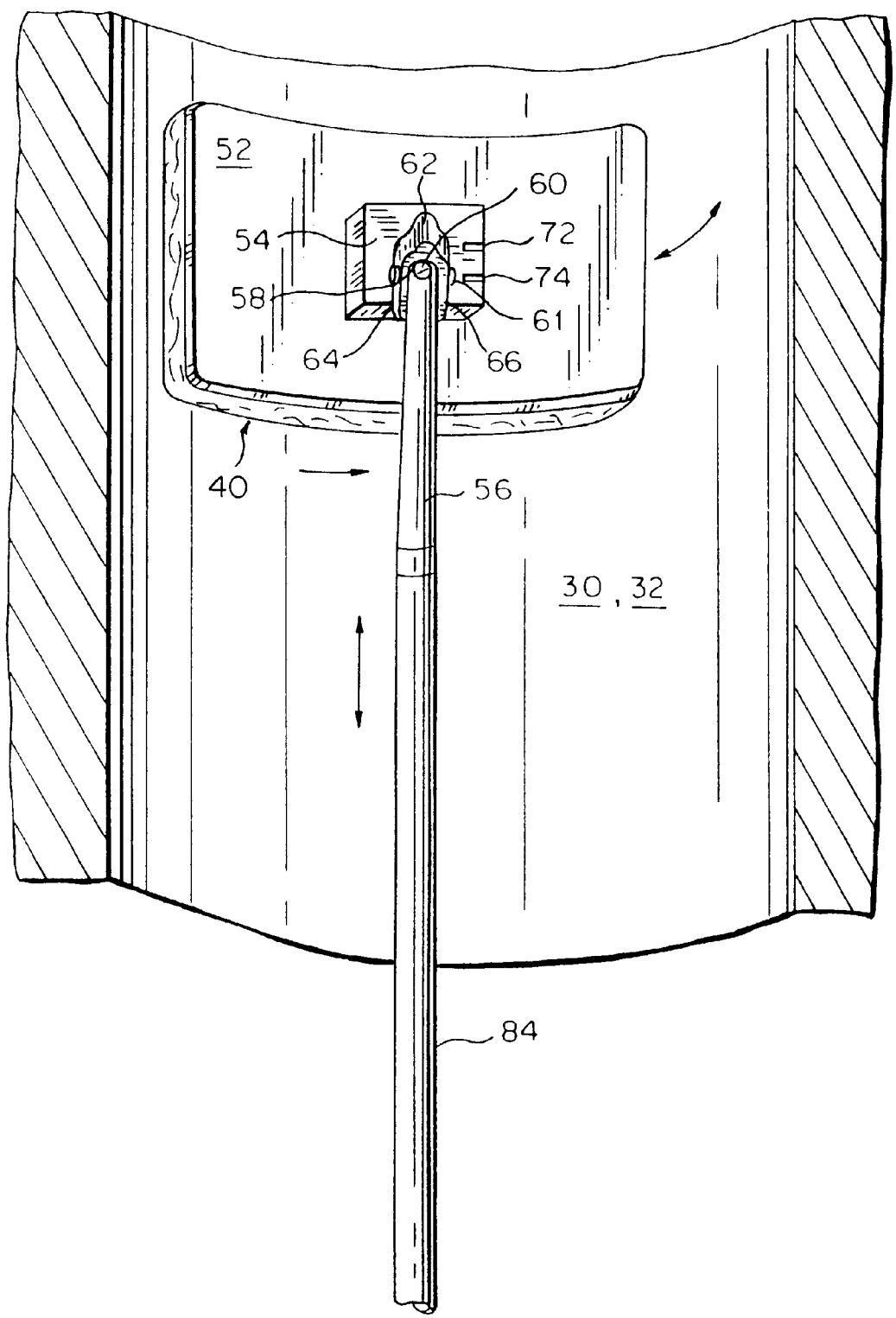
FIG. 11 is a perspective view showing the first cleaning implement cleaning the side walls of a bore of an MRI machine.
Figure 12:
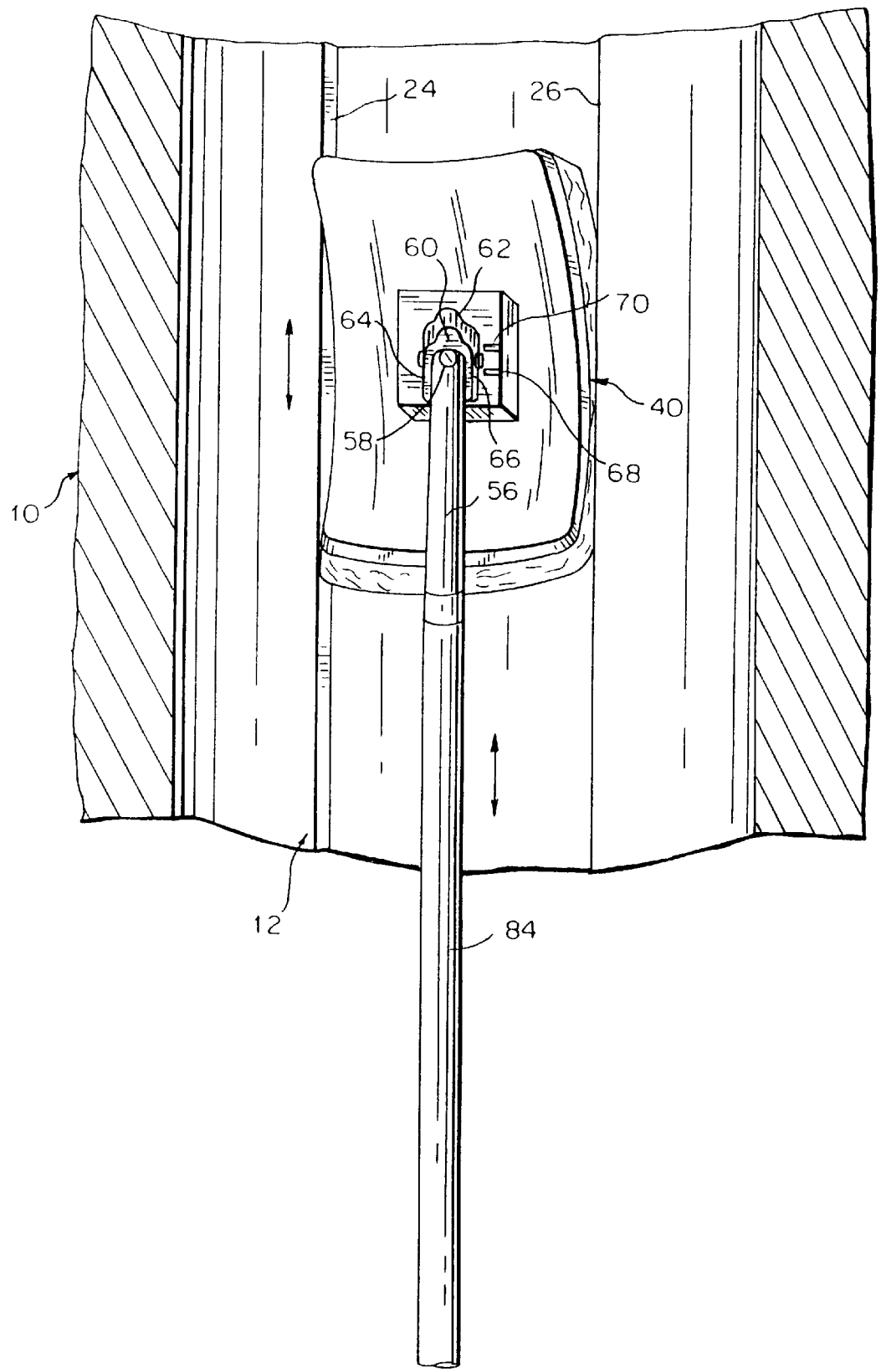
FIG. 12 is a perspective view of a first cleaning implement cleaning the ceiling of the bore of an MRI machine.

Referring now to FIG. 11, cleaning head 50 is shown disposed with respect to the handle 84 in a position for cleaning the side walls 30 or 32. As is seen in FIG. 12, the cleaning head 50 has been rotated 90° for cleaning the top wall 28 between the ribs 24 and 26.

Figure 13:
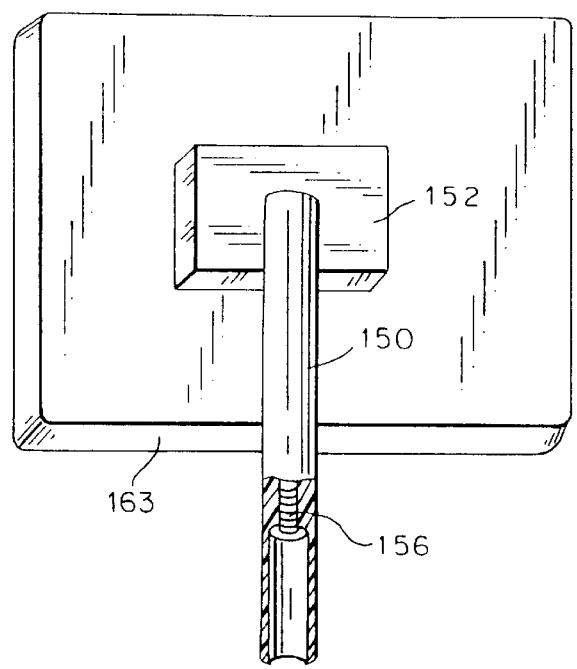
FIG. 13 is a back view of a second cleaning implement for cleaning the track or floor of an MRI machine.
Figure 14:
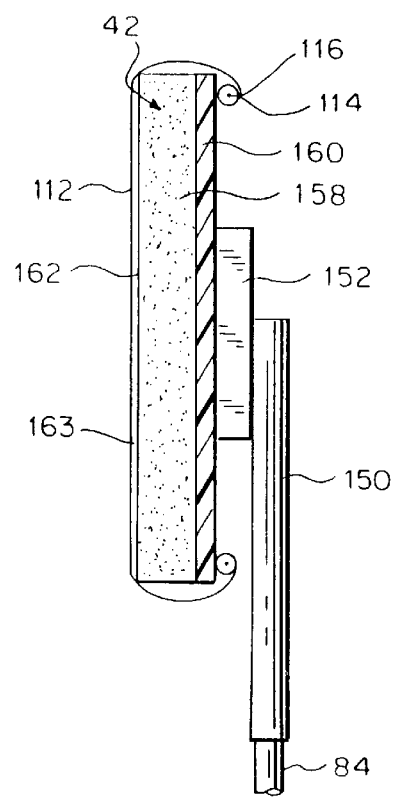
FIG. 14 is a side view of the second cleaning implement.

Referring now to FIGS. 13 and 14 where the second cleaning element 42 is shown, it is seen that the second cleaning element 42 has a socket 150 fixed to a boss 152 for receiving the handle 84 with a threaded nut 156 fixed within the socket. The second cleaning element 42 has a sponge element 158 mounted on a mounting plate 160 using the VELCRO® fastener approach of FIG. 4 and utilizes the disposable cleaning cloth covers 112 of FIGS. 5 and 6. The sponge element 158 has a flat face 162 covered with a flexible liquid impermeable barrier 163 for complementing the floor 16 of the tunnel 12 (see FIG. 1).

It may be necessary to use the cleaning elements 40 and/or 42 as sponge elements in which the waterproof coverings 110 and 163 are removed. According to a detachable squeeze plate 170 is provided which has hinge elements 172 that removably couple with hinge elements 174 on the mounting plates 52 and 160.

All of the aforedescribed components are of non-ferrous materials so as not to interact with the magnetic field of the MRI machine 10 which is being cleaned and/or sanitized. Preferably, the materials are resinous materials (plastics).

By the term "sponge" what is meant is a deformable, resilient body which is relatively soft and restores its shape after being deformed.

FIGS. 16 and 17 are photographs of the cleaning implement according to the present invention. Each of the other drawing FIGS. include the structure and design characteristics of FIGS. 16 and 17 and should be viewed in the light thereof.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of sanitizing a bore of an MRI machine wherein the bore has arcuate side surfaces and a ceiling comprising:

applying a sanitizing liquid to arcuate side surfaces of the bore with a first sponge element mounted on an elongated handle, wherein the sponge element has an application surface configured as a sector of a sphere having a radius equal to the radius of the bore;

rotating the sponge element 90°: and applying the sanitizing liquid to the ceiling of the bore with the first sponge element after the sponge element has been rotated 90° whereby the bore of the MRI machine is sanitized.

2. The method of claim 1 further including removing the first sponge element and replacing the first sponge element with a second sponge element having a planar application surface and applying sanitizing liquid to a flat floor of the bore with the second sponge element.

3. A method for protecting the health of patients inserted into the bore of an MRI machine for scanning by the MRI machine comprising the steps of:

a) inserting a patient in the bore;

b) sanitizing the bore after scanning the patient and removing the patient from the bore by swabbing the bore with a sanitizing agent, and c) repeating step b) after scanning another patient and removing that patient from the bore, whereby the health of the patients being scanned is protected by minimizing exposure to infectious agents.

4. The method of claim 3, wherein sanitizing the bore comprises applying a sanitizing agent to walls, ceiling and floor of the bore with a disposable wiping member mounted on a deformable support having an elongated handle.

* * * * *